(12) United States Patent
Kovesdi (10) Patent No.: US 6,753,321 B2
(45) Date of Patent: Jun. 22, 2004

(54) METHOD OF MODULATING NEOVASCULARIZATION

(75) Inventor: Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/952,498

(22) Filed: Sep. 14, 2001

(65) Prior Publication Data

US 2003/0053989 A1 Mar. 20, 2003

Related U.S. Application Data

(60) Provisional application No. 60/233,001, filed on Sep. 15, 2000.

(51) Int. Cl.$^7$ ............................................. A61K 48/00
(52) U.S. Cl. .................... 514/44; 424/93.2; 435/320.1; 435/455; 435/456
(58) Field of Search .................... 514/44; 424/93.2; 435/320.1, 455, 456

(56) References Cited

U.S. PATENT DOCUMENTS 5,972,338 A   10/1999   Godowski et al. ....... 424/185.1

FOREIGN PATENT DOCUMENTS

| | | |
|---|---|---|
| EP | 0 819 758 A | 1/1998 |
| EP | 1016726 A | 7/2000 |
| EP | 1016727 A | 7/2000 |
| WO | WO 96/21015 A | 7/1996 |
| WO | WO 97/23613 A | 7/1997 |
| WO | WO 97/41844 A | 11/1997 |
| WO | WO 98/05779 A | 2/1998 |
| WO | WO 99/40193 A | 8/1999 |
| WO | WO 99/47690 A | 9/1999 |
| WO | WO 00/01410 A | 1/2000 |
| WO | WO 00/02579 A | 1/2000 |
| WO | WO 00/03014 A | 1/2000 |
| WO | WO 00/40740 A | 7/2000 |
| WO | WO 00/41712 A | 7/2000 |
| WO | WO 00/52617 A | 9/2000 |
| WO | WO 00/57901 A | 10/2000 |
| WO | WO 02/02148 A | 1/2002 |

OTHER PUBLICATIONS

Anonymous, "Collateral Therapeutics Appoints John F. Warner Ph.D. Vice President of Technology," Collateral Therapeutics, Inc. Press Release (May 9, 2000). [http://www.shareholder.com/cltx/news/20000509–16062.htm].
Anonymous, "Collateral Therapeutics Creates First Combination FGV/VEGF Gene for Non–Surgical Cardiovascular Angiogenesis," Collateral Therapeutics, Inc. Press Release (Nov. 8, 1999). [http:/www.shareholder.com/cltx/news/19991108–11887.htm].
Anonymous, "Scientists Find Protein Can Protect New Blood Vessels From Leaking—Promising Complement to Growth Stimulant," *Science Daily Magazine* (Dec. 24, 1999). [http://www.sciencedaily.com/releases/1999/12/991224090647.htm].
Chae et al., *Arterioscler. Thromb. Vasc. Biol.*, 20, 2573–2578 (Dec. 2000).
Huang et al., *Biochem. Biophys. Res. Comm.*, 264 (1), 133–138 (Oct. 14, 1999).
Peters, *Circ. Res.*, 83(3), 342–343 (Aug. 10, 1998).
Thurston et al., *Nature Med.*, 6 (4), 460–463 (Apr. 2000).
Asahara et al., *Circ. Res.*, 83 (3), 233–240 (Aug. 1998).
Christenson et al., *Stroke*, 29 (7), 1411–1416 (Jul. 1998).
Jain et al., *Nat. Med.*, 6 (2), 131–132 (Feb. 2000).
Penta et al., *J. Biol. Chem.*, 274 (16), 11101–11109 (Apr. 16, 1999).
Relf et al., *Cancer Res.*, 57 (5), 963–969 (Mar. 1, 1997).

*Primary Examiner*—Scott D. Priebe
(74) *Attorney, Agent, or Firm*—Leydig, Voit & Mayer, Ltd.

(57) ABSTRACT

The present invention provides a method of modulating neovascularization in an animal. The method comprises administering to the animal two or more nucleic acid sequences, each nucleic acid sequence encoding at least one angiogenesis-modulation factor that acts upon a different angiogenic process, such that the nucleic acid sequences are expressed to produce the angiogenesis-modulation factors to modulate neovascularization in the animal. Modulating neovascularization includes the induction of neovascularization or, in the alternative, the inhibition or reduction of neovascularization.

22 Claims, 2 Drawing Sheets

METHOD OF MODULATING NEOVASCULARIZATION

CROSS REFERENCE TO RELATED PATENT APPLICATIONS

This patent application claims the benefit of U.S. Provisional Patent Application No. 60/233,001, filed on Sep. 15, 2000.

TECHNICAL FIELD OF THE INVENTION

This invention pertains to a method of modulating neovascularization in an animal.

BACKGROUND OF THE INVENTION

Neovascularization, or the formation of new blood vessels, is a highly complex and tightly regulated biological process. Neovascularization is normally not continuously required on a large scale in adult animals, thus the process for forming blood vessels is often quiescent except in instances of injury and wound repair. When vascularization is not stringently controlled, serious pathologies can result. For example, reduced vascularization of target tissues is associated with ischemic damage, vascular diseases, necrosis, and muscle wasting. Increased vascularization is associated with, for instance, tumor growth, edema, and diseases of eye, such as diabetic retinopathy and the exudative form of age-related macular degeneration, which are major causes of blindness worldwide.

Several strategies for controlling vascularization have been proposed. Angiogenic or anti-angiogenic proteins have been administered to an animal to modulate neovascularization. However, it is difficult to target the administration of proteins to tissues such that widespread neovascularization does not occur. In addition, the half-life of some angiogenesis-influencing factors is relatively low, thereby complicating administration of appropriate dosages of peptides to achieve a desired effect. Delivery of an angiogenic or an anti-angiogenic agent to target tissues has also been achieved using gene transfer methods with encouraging results. For example, delivery of vascular endothelial growth factor (VEGF) has promoted improved perfusion of cardiac tissue and ischemic limbs (see, for example, Isner et al., *The Lancet*, 348, 370–373 (1996). While perfusion of the target tissue is improved, a more efficient means of modulating neovascularization is needed. In addition, some factors have reduced efficacy under certain conditions. For example, preclinical data suggest that VEGF is less effective in aged individuals.

In view of the above, there exists a need in the art for an alternative and efficient means of modifying vascularization in an animal. The present invention provides such a method. This and other advantages of the present invention, as well as additional inventive features, will be apparent from the description of the invention provided herein.

BRIEF SUMMARY OF THE INVENTION

The present invention provides a method of modulating neovascularization in an animal. The method comprises administering to the animal two or more nucleic acid sequences, each nucleic acid sequence encoding at least one angiogenesis-modulation factor that acts upon a different angiogenic process. Each nucleic acid sequence is under the control of separate promoters having different expression profiles. The nucleic acid sequences are expressed to produce the angiogenesis-modulation factors to modulate neovascularization in the animal. The angiogenesis-modulation factor can be an angiogenesis-promoting factor such that neovascularization is induced in the animal. Alternatively, the angiogenesis-modulation factor is an angiogenesis inhibitor and neovascularization is inhibited or reduced in the animal.

DETAILED DESCRIPTION OF THE INVENTION

The present invention provides a method of modulating neovascularization in an animal. The method comprises administering to the animal two or more nucleic acid sequences, each nucleic acid sequence encoding at least one angiogenesis-modulation factor that acts upon a different angiogenic process, such that the nucleic acid sequences are expressed to produce the angiogenesis-modulation factors to modulate neovascularization in the animal. Modulating neovascularization includes the induction of neovascularization or, in the alternative, the inhibition or reduction of neovascularization.

Angiogenesis-modulation factors are gene products that affect the formation of new blood vessels. Angiogenesis-modulation factors can influence the actual generation of new blood vessels, as well as the quality of the blood vessels. The angiogenesis-modulation factors produced by the expression of the nucleic acid sequences act upon different biological processes. In other words, the angiogenesis-modulation factors desirably have different mechanisms of modulating neovascularization. Angiogenesis is a complex biological phenomenon that relies on several controlled angiogenic processes. Neovascularization begins with the enzymatic breakdown of the basement membrane of a blood vessel. Endothelial cells migrate to the area of degradation and invade the surrounding extracellular matrix. The invading endothelial cells proliferate to form an elongated column of cells. A lumen then forms within the solid cell column, thereby forming a vessel. Lumen formation involves the differentiation of endothelial cells and the formation of the basement membrane in the new structure. Eventually, the newly formed vessel structure connects with an existing blood vessel (see, for example, Fotsis et al., *J. Nutr.*, 125: 790S–797S (1995)). The newly formed vessel, as well as existing vessels, also can divide to form branches and capillary networks. The division of existing vessels to form capillary networks is called non-sprouting angiogenesis or intussusception. The above-described processes are dependent on signaling molecules and chemical messengers to regulate and coordinate the biological events such that functional blood vessels are produced. Thus, as used herein, any biological process involved in the formation of new blood vessels, e.g., basement membrane breakdown, cell proliferation, cell migration, vessel wall maturation, lumen formation, vessel dilatation, production of mediators, branching of vessels, etc., is an "angiogenic process."

Preferably, the angiogenesis-modulating factors modulate different angiogenic processes by acting upon different target molecules. Target molecules refer to, for example, receptors (e.g., growth factor receptors), intracellular signaling molecules, genes, RNA transcripts, and chemical mediators. By interacting with different target molecules, two or more angiogenesis-modulating factors influence neovascularization on multiple fronts, which provides a more complete biological response.

In addition, as the angiogenesis-modulation factors preferably act on different target molecules, each angiogenesis-modulation factor desirably acts upon different cellular signal transduction pathways. Different angiogenic processes rely on different effector molecules and signal transduction pathways for regulation. For example, growth factors such as a vascular endothelial growth factor (VEGF), fibroblast growth factor (FGF), and platelet derived growth factor (PDGF) act through a tyrosine kinase family receptor system to transmit signals to the cell nucleus. Growth factors, growth factor receptors, and their corresponding signal transduction pathways are described in the *Handbook of Experimental Pharmacology*, Spawn & Roberts, Eds., V95, Springer-Verlag (1990). Transcription factors such as HIF-1α and PR39 do not act through tyro sine kinase receptors but, instead, act directly on DNA to promote the production of positive regulators of angiogenesis. HBNF acts by up-regulating the production of urokinase, thereby promoting angiogenesis. Similarly, soluble growth factor receptors inhibit neovascularization by blocking signaling through growth factor receptors, while pigment epithelium derived factor (PEDF) is a serine protease inhibitor that most likely influences cell-cell or cell-extracellular matrix interactions. Angiostatin works through signal transduction pathways to achieve mitotic arrest. Thus, each class of angiogenesis-modulation factor has different mechanisms of action by acting through different target molecules.

The present inventive method can be used to induce or promote neovascularization. By "induction of neovascularization" is meant that angiogenesis is either initiated or enhanced. Therefore, for example, when neovascularization is not occurring, the present method provides for initiation of neovascularization. However, if neovascularization is already present, the present method provides a means by which the level of neovascularization is enhanced or heightened. When induction of neovascularization is desired, the angiogenesis-modulation factor is an angiogenesis-promoting factor, e.g., a gene product that aids in the formation and/or quality of new blood vessels. Preferably, a greater degree of neovascularization is induced by the present inventive method compared to neovascularization resulting from administration of one of the nucleic acid sequences alone.

With respect to induction of neovascularization, the present invention is predicated, in part, on the surprising and unexpected discovery that the use of two nucleic acid sequences, each encoding a different angiogenic-promoting factor that acts upon a different angiogenic process, can induce a greater biological effect than achieved using the maximal levels of angiogenic agents in previously described methods. For example, it was previously believed that the greatest level of angiogenesis possible is achieved by using the maximal dose of, for example, VEGF. However, the present invention provides a method which achieves enhanced neovascularization (an increase in maximal angiogenesis) and a better biological effect. Ideally, the combination of nucleic acid sequences demonstrates greater than 100% of the angiogenic activity of any one of the nucleic acid sequences (monotherapy) alone. Preferably, the combination of nucleic acid sequences as used in the present inventive method demonstrates at least 110%, most preferably 120%, of the angiogenic activity of any one of the nucleic acid sequences (monotherapy) alone.

Angiogenesis-modulating factors can influence the amount or size of blood vessels formed, or can influence the quality of the newly formed vessels. For instance, instead of increasing the number of new vessels, an angiogenesis-promoting factor can promote better conduction through vessels. Desirably, the angiogenesis-promoting factors used in the present inventive method include, for example, an endothelial mitogen, a factor associated with endothelial migration, a factor associated with vessel wall maturation, a factor associated with vessel wall dilatation, a factor associated with extracellular matrix degradation, or a transcription factor. Endothelial mitogens include, for instance, a vascular endothelial growth factor (VEGF), fibroblast growth factors (FGF, e.g., aFGF, bFGF, and FGF-4), platelet derived growth factor (PDGF), placental growth factor (PLGF), angiogenin, hepatocyte growth factor (HGF), tumor growth factor-beta (TGF-B), connective tissue growth factor (CTGF), and epidermal growth factor (EGF). Endothelial migration can be induced by, for example, Del-1. Factors associated with vessel wall maturation include, but are not limited to, angiopoietins (Ang, e.g., Ang-1 and Ang-2), tumor necrosis factor-alpha (TNF-α), midkine (MK), COUP-TFII, and heparin-binding neurotrophic factor (HBNF, also known as heparin binding growth factor). Vessel wall dilatators include, for example nitric oxide synthase (e.g., eNOS and iNOS) and monocyte chemoattractant protein-1 (MCP-1). Extracellular matrix degradation is promoted by, for instance, Ang-2, TNF-α, and MK. Suitable transcription factors include, for instance, HIF-1α and PR39. Other angiogenesis-promoting factors include activin binding protein (ABP) and tissue inhibitor of metalloproteinase (TIMP). Clotting factors, such as tissue factor, FVIIa, FXa, thrombin, and activators of PAR1, PAR2, and PAR3 receptors, also are thought to play a role in angiogenesis (see, for example, Carmeliet et al., *Science*, 293, 1602 (2001)). Additional angiogenic-promoting factors are described in U.S. patent application Ser. No. 09/832,355.

Angiogenesis-promoting factors are variously described in U.S. Pat. No. 5,194,596 (Tischer et al.), U.S. Pat. No. 5,219,739 (Tischer et al.), U.S. Pat. No. 5,338,840 (Bayne et al.), U.S. Pat. No. 5,532,343 (Bayne et al.), U.S. Pat. No. 5,169,764 (Shooter et al.), U.S. Pat. No. 5,650,490 (Davis et al.), U.S. Pat. No. 5,643,755 (Davis et al.), U.S. Pat. No. 5,879,672 (Davis et al.), U.S. Pat. No. 5,851,797 (Valenzuela et al.), U.S. Pat. No. 5,843,775 (Valenzuela et al.), and U.S. Pat. No. 5,821,124 (Valenzuela et al.); International Patent Applications WO 95/24473 (Hu et al.) and WO 98/44953 (Schaper); European Patent Documents 476 983 (Bayne et al.), 506 477 (Bayne et al.), and 550 296 (Sudo et al.); Japanese Patent Documents 1038100, 2117698, 2279698, and 3178996; J. Folkman et al., *Nature*, 329, 671 (1987); Fernandez et al., *Circulation Research*, 87, 207–213 (2000), and Moldovan et al., *Circulation Research*, 87, 378–384 (2000). Preferably, at least one of the nucleic acid sequences encodes a tissue-specific angiogenic factor, most preferably an endothelial-specific angiogenic factor, such as VEGF.

While any nucleic acid sequence, e.g., DNA, encoding an angiogenesis-promoting gene product operably linked to suitable expression signals can be used within the context of the present invention, preferably one of the angiogenesis-promoting factors is a VEGF protein or a biologically active (e.g., neovascularization-promoting) fragment thereof. More preferably, the angiogenic gene product is $VEGF_{121}$, $VEGF_{145}$, $VEGF_{165}$, $VEGF_{189}$, $VEGF_{206}$, or a mammalian counterpart, which are variously described in U.S. Pat. No. 5,332,671 (Ferrara et al.); U.S. Pat. No. 5,240,848 (Keck et al.); and U.S. Pat. No. 5,219,739 (Tischer et al.). Most preferably, because of their higher biological activity, one of the angiogenesis-promoting factors is $VEGF_{121}$ or $VEGF_{165}$, particularly $VEGF_{121}$. A notable difference between $VEGF_{121}$ and $VEGF_{165}$ is that $VEGF_{121}$ does not bind to heparin with a high degree of affinity, as does $VEGF_{165}$. Generally, VEGF moieties are advantageous over other angiogenic peptides because VEGF proteins do not induce the growth of tissues not involved in the production of new vasculature. Other suitable VEGF peptides for use in the present inventive method are VEGF-II, VEGF-C, and the like. In a preferred embodiment, at least one nucleic acid sequence of the present method encodes VEGF or a biologically active fragment thereof and at least one other nucleic acid sequence encodes an angiogenesis-promoting factor other than VEGF or a biologically active fragment thereof. When the angiogenesis-promoting factors are produced, desirably, a greater degree of neovascularization is induced compared to neovascularization resulting from administration of a nucleic acid sequence encoding VEGF or a biologically active fragment thereof alone.

Figure 1:
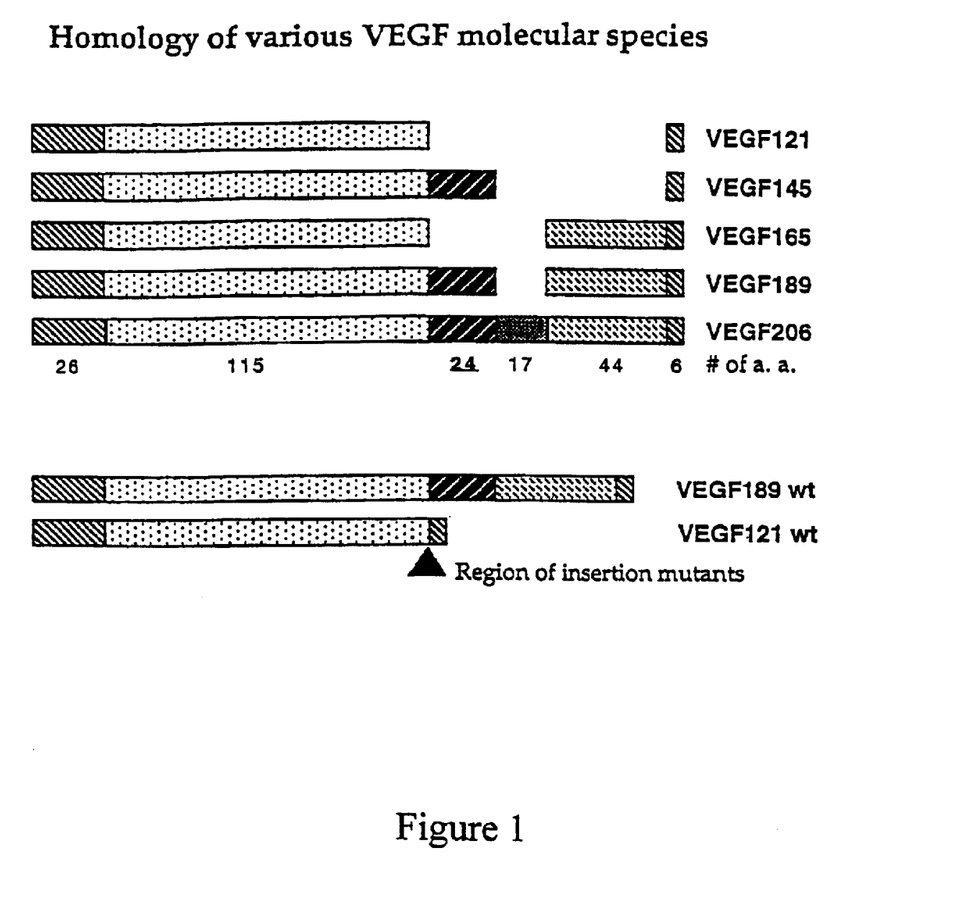
FIG. 1 is a schematic illustrating the homology of various molecular species of vascular endothelial growth factor (VEGF).
Figure 2:
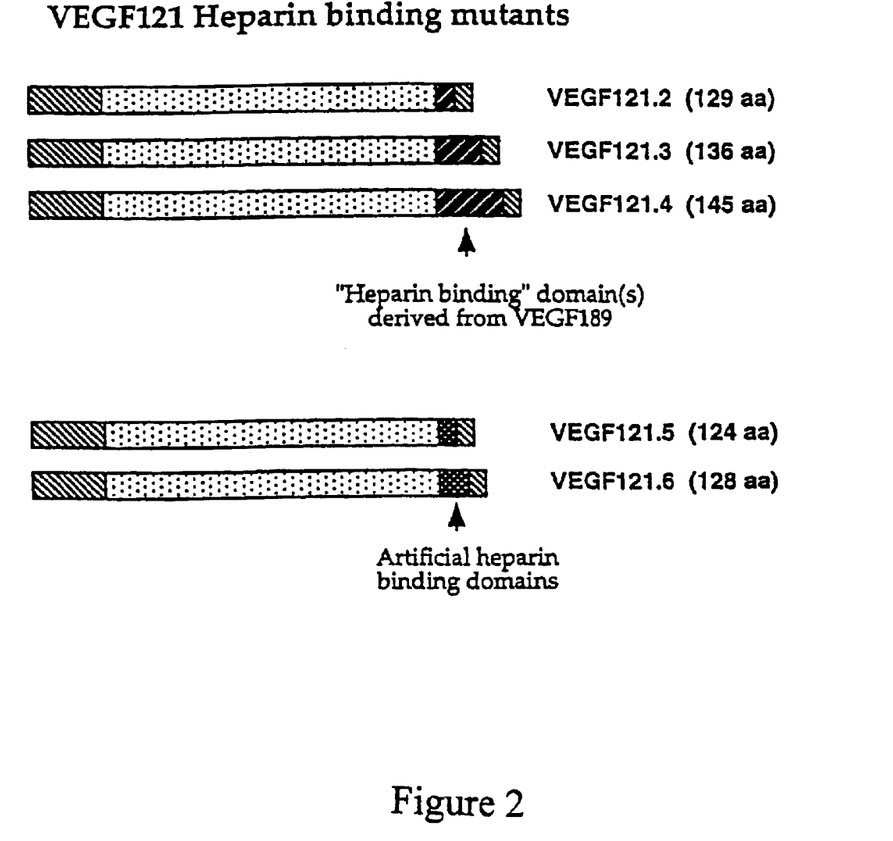
FIG. 2 is a schematic of $VEGF_{121}$ heparin binding variant peptides.

In addition to the VEGF proteins described above, variants, mutants, or chimeras of a VEGF protein, as well as any angiogenesis-modulation gene product, can be used in the present inventive method. For example, variants of the $VEGF_{121}$ peptide that comprise various segments of the heparin-binding domain of $VEGF_{189}$ (FIG. 2) can be used. VEGF chimeric peptides comprising artificial heparin-binding domains are also appropriate for use in the present inventive method. The heparin-binding domains can be inserted within the angiogenic peptide, or associated with the N- or C-terminus of the peptide, as appropriate. The option of modifying the heparin-binding activity of VEGF peptides provides an addition means of controlling angiogenic activity.

Alternatively, the angiogenesis-modulating factor can be an angiogenesis inhibitor such that, when produced, neovascularization is inhibited or reduced in the animal. By "angiogenesis inhibitor" is meant any gene product that prevents or ameliorates neovascularization. One of ordinary skill in the art will understand that complete prevention or amelioration (reduction) of neovascularization is not required in order to obtain a biological effect. Therefore, the present inventive method contemplates both partial and complete prevention and amelioration of angiogenesis. In the present inventive method, the angiogenesis inhibitors act upon different angiogenic processes. Therefore, angiogenesis inhibitors can, for example, inhibit cell proliferation, cell migration, vessel formation, extracellular matrix degradation, production of mediators, and the like. Angiogenesis inhibitors also can be antagonists for angiogenesis-promoting agents, such that the angiogenesis-promoting factors are neutralized (see, for example, Sato, *Proc. Natl. Acad. Sci. USA*, 95, 5843–5844 (1998)).

Angiogenesis inhibitors suitable for use in the present invention include, for instance, anti-angiogenic factors, cytotoxins, apoptotic factors, anti-sense molecules specific for an angiogenic factor, ribozymes, receptors for an angiogenic factor, an antibody that binds an angiogenic factor, and an antibody that binds a receptor for an angiogenic factor.

Anti-angiogenic factors, cytotoxins, and apoptotic factors work to inhibit angiogenesis by directly acting upon cellular functions associated with neovascularization. The anti-angiogenic factors contemplated for use in the present invention include pigment epithelium-derived factor (PEDF), angiostatin, thrombospondin, protamine, vasculostatin, endostatin, platelet factor 4, heparinase, interferons (e.g., INFα), and the like. One of ordinary skill in the art will appreciate that any anti-angiogenic factor can be modified or truncated and retain anti-angiogenic activity. As such, active fragments of anti-angiogenic agents (i.e., those fragments having biological activity sufficient to inhibit angiogenesis) are suitable for use in the present inventive methods. Hyaluronic acid is also known to inhibit endothelial cell proliferation and, therefore, is an appropriate anti-angiogenic agent for use in the present method (*Heart Development*, Harvey & Rosenthal, eds., Academic Press, New York, 1999, see Chapter 14). Anti-angiogenic agents are further discussed in U.S. Pat. No. 5,840,686; International Patent Applications WO 93/24529 and WO 99/04806; Chader, *Cell Different.*, 20, 209–216 (1987); Dawson et al, Science, 285, 245–248 (1999); and Browder et al, J. Biol. Chem., 275, 1521–1524 (2000).

Numerous cytotoxins and apoptotic factors are known in the art and include, for example, p53, Fas, Fas ligand, Fas-associating protein with death domain (FADD), caspase-3, caspase-8 (FLICE), caspase-10, Apo2L, tumor necrosis factor (TNF)-R1, IκB, ΔIκB, receptor-interacting protein (RIP)-associated ICH-1/CED-3-homologous protein with a death domain (RAIDD), TNF-related apoptosis-inducing ligand (TRAIL), DR4, DR5, a cell death-inducing coding sequence of Bcl-2 which comprises an N-terminal deletion, a cell death-inducing coding sequence of Bcl-x which comprises an N-terminal deletion, Bax, Bak, Bid, Bad, Bik, Bif-2, c-myc, Ras, Raf, PCK kinase, AKT kinase, Akt/PI(3)-kinase, PITSLRE, death-associated protein (DAP) kinase, RIP, JNK/SAPK, Daxx, NIK, MEKK1, ASK1, PKR, and mutants thereof (e.g., dominant negative mutants thereof and dominant positive mutants thereof), and fragments thereof (e.g., active domains thereof), and combinations thereof. Apoptotic, cytotoxic, and cytostatic transcription factors can be used in the present method and include, for example, E2F transcription factors and synthetic cell cycle-independent forms thereof, an AP1 transcription factor, an AP2 transcription factor, an SP transcription factor (e.g., an SP1 transcription factor), a helix-loop-helix transcription factor, a DP transcription factor (e.g., DP1, DP2, and DP3), and mutants thereof (e.g., dominant negative mutants thereof and dominant positive mutants thereof), and fragments thereof (e.g., active domains thereof), and combinations thereof. Apoptotic, cytotoxic, and cytostatic viral proteins include, for example, an adenoviral E1A product, an adenoviral E4/ORF6/7 product, an adenoviral E4/ORF4 product, a cytomegalovirus (CMV) product (e.g., CMV-thymidine kinase (CMV-TK)), a herpes simplex virus (HSV) product (e.g., HSV-TK), a human papillomavirus (HPV) product (e.g., HPVX), and mutants thereof (e.g., dominant negative mutants thereof and dominant positive mutants thereof), and fragments thereof (e.g., active domains thereof), and combinations thereof. Cytotoxins and apoptotic factors are particularly useful in inhibiting cell proliferation, an important angiogenic process. Suitable cytotoxins and apoptotic agents can be identified using routine techniques, such as, for instance, cell growth assays and the Tunnel assay, respectively.

Anti-sense molecules, ribozymes, soluble receptors, and antibodies to angiogenic factors and receptors can be considered "antagonistic" angiogenesis inhibitors, as they sequester away positive regulators of neovascularization. An anti-sense molecule specific for an angiogenic factor should generally be substantially identical to at least a portion, preferably at least about 20 continuous nucleotides, of the nucleic acid encoding the angiogenic factor to be inhibited, but need not be identical. The anti-sense nucleic acid molecule can be designed such that the inhibitory effect applies to other proteins within a family of genes exhibiting homology or substantial homology to the nucleic acid. The introduced anti-sense nucleic acid molecule also need not be full-length relative to either the primary transcription product or fully processed mRNA. Generally, higher homology can be used to compensate for the use of a shorter sequence. Antisense phosphorothiotac oligodeoxynucleotides (PS-ODNs) is exemplary of an anti-sense molecule specific for an angiogenic factor.

Ribozymes can be designed that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloffet al., *Nature*, 334, 585–591 (1988). Preferably, the ribozyme comprises at least about 20 continuous nucleotides complementary to the target sequence on each side of the active site of the ribozyme.

Receptors specific for angiogenic factors inhibit neovascularization by sequestering positive regulators (e.g., growth factors) away from functional receptors capable of promoting a cellular response. For example, soluble VEGF-R1 (flt-1), soluble VEGF-R2 (flk/kdr), and soluble VEGF-R3 (flt-4) receptors, as well as VEGF-receptor-chimeric proteins, compete with VEGF receptors on vascular endothelial cells to inhibit endothelial cell growth (Aiello, *PNAS*, 92, 10457 (1995)). Also contemplated are angiogenic factor-specific antibodies and fragments thereof (e.g., Fab, F(ab')$_2$, and Fv) that neutralize angiogenic factors or bind receptors for angiogenic factors.

In a preferred embodiment, at least one nucleic acid sequence encodes a soluble VEGF-R1 receptor and at least one nucleic acid sequence encodes PEDF. VEGF-R1 receptors bind VEGF such that the growth factor is unable to interact with functional receptors to promote endothelial cell proliferation. PEDF, on the other hand, is a protease that interferes with cell-cell signaling or the interaction of cells with their environment such that cell migration is blocked. Use of a nucleic acid encoding a soluble receptor in conjunction with a nucleic acid encoding PEDF blocks neovascularization by negatively regulating different angiogenic processes.

In the present method, two or more nucleic acids, each encoding at least one angiogenesis-modulation factor, are administered to an animal to modulate neovascularization in the animal. The nucleic acids can comprise DNA, RNA, or a DNA-RNA hybrid, although DNA is preferred. The nucleic acids can be obtained from any source, and can comprise, for example, genomic DNA, cDNA, or synthetic DNA. At least two nucleic acids encoding different angiogenesis-modulation factors are employed in the present method, although more than two nucleic acids (e.g., 3, 4, 5, 6 or more nucleic acids) can be used. The nucleic acid sequences desirably are present on an expression vector suitable for introducing exogenous nucleic acids into host cells. The nucleic acid sequences can be present on separate expression vectors or, in the alternative, can be present on a single expression vector.

Suitable expression vectors for use in the present inventive method include, but are not limited to, naked DNA molecules (e.g., plasmids), DNA complexed with transfection-facilitators (e.g., liposomes), and viral vectors, such as adeno-associated virus (AAV)-based vectors, retroviral vectors, herpes simplex virus (HSV)-based vectors, AAV-adenoviral chimeric vectors, and adenovirus-based vectors. Any of these expression vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Preferably, the expression vector of the present inventive method is a viral vector; more preferably, the expression vector is an adenoviral vector. Adenovirus (Ad) is a 36 kb double-stranded DNA virus that efficiently transfers DNA in vivo to a variety of different target cell types. Adenoviral vectors can be produced in high titers and can efficiently transfer DNA to replicating and non-replicating cells, which is advantageous in modulating neovascularization. Newly transferred genetic material remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors are an interesting option for use in the present invention.

In the context of the present invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Manassis, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, however, an adenovirus is of serotype 2 or 5.

Regions of the adenoviral genome (e.g., the E3 region) can optionally be deleted in order to provide space for insertion of exogenous nucleic acids. In addition, regions of the adenoviral genome can be deleted or altered in order to interfere with viral replication. The adenoviral vector used in the present inventive method is preferably deficient in at least one gene function required for viral replication, thereby resulting in a "replication-deficient" adenoviral vector. Preferably, the adenoviral vector is deficient in at least one essential gene function of the E1 region (e.g., deficient in at least part of the E1a region and/or at least part of the E1b region) of the adenoviral genome. In addition to a deficiency in the E1 region, the recombinant adenovirus also can have a mutation in the major late promoter (MLP), as discussed in International Patent Application WO 00/00628. More preferably, the vector is deficient in at least one essential gene function of the E1 region and at least part of the E3 region.

Preferably, the adenoviral vector is "multiply deficient," meaning that the adenoviral vector is deficient in one or more essential gene functions required for viral replication in each of two or more regions. For example, the aforementioned E1-deficient or E1-, E3-deficient adenoviral vectors can be further deficient in at least one essential gene of the E2 region (e.g., the E2a region) and/or the E4 region. Adenoviral vectors deleted of the entire E4 region can elicit lower host immune responses. Therefore, the adenoviral vector used in the present inventive method can lack all or part of the E1 region, all or part of the E2 region, all or part of the E3 region, and/or all or part of the E4 region, and any variation thereof. Suitable replication-deficient adenoviral vectors are disclosed in U.S. Pat. Nos. 5,851,806 and 5,994,106 and International Patent Applications WO 95/34671 and WO 97/21826.

With respect to E4 deficient adenoviral vectors, it has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0. In view of the above, a nucleic acid sequence encoding a trans-acting factor that modulates the persistence of expression of a nucleic acid sequence is preferably provided, whether present on the adenoviral vector or supplied by a second expression vector. The use of trans-acting factors is further described in U.S. Pat. No. 6,225,113 and International Patent Application WO 00/34496.

It should be appreciated that the deletion of different regions of the viral vector, e.g., the adenoviral vector, once administered to an animal, can alter the properties of the viral vector. For example, an adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent or chronic neovascularization.

Similarly, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, pIX, pIIIa, or hexon, insertions of various native or non-native ligands into portions of the coat protein, and the like. Manipulation of the coat protein can broaden the range of cells infected by a viral vector or enable targeting of a viral vector to a specific cell type. One direct result of manipulation of the viral coat is that the virus, preferably, the adenovirus, can bind to and enter numerous cell types which a virus comprising wild-type coat protein typically cannot enter or can enter with only a low efficiency. In some embodiments, manipulation of the viral coat allows the virus to efficiently bind to a broader range of eukaryotic cells than a wild-type virus coat, such as described in International Patent Application WO 97/20051. In other embodiments, the viral coat is manipulated such that the virus is "targeted" to a particular cell type, e.g., those cells expressing unique receptors. Suitable modifications to a viral vector, specifically an adenoviral vector, such as, for example, those described herein, are described in U.S. Pat. Nos. 5,559,099; 5,731,190; 5,712,136; 5,770,442; 5,846,782; 5,962,311; 5,965,541; 6,057,155; 6,127,525; and 6,153,435; and International Patent Applications WO 96/07734, WO 96/26281, WO 97/20051, WO 98/07865, WO 98/07877, WO 98/40509, WO 98/54346, and WO 00/15823.

The construction of viral vectors is well understood in the art. Adenoviral vectors can be constructed and/or purified using the methods set forth, for example, in U.S. Pat. No. 5,965,358 and International Patent Applications WO 98/56937, WO 99/15686, WO 99/54441 and WO 00/12765. Adeno-associated viral vectors can be constructed and/or purified using the methods set forth, for example, in U.S. Pat. No. 4,797,368 and Laughlin et al., *Gene*, 23, 65–73 (1983).

Preferably, the nucleic acid sequences encoding different angiogenic-modulation factors are operably linked to regulatory sequences necessary for expression, i.e., a promoter. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. A promoter can be native or non-native to the nucleic acid sequence to which it is operably linked. Two or more nucleic acid sequences can be under the control of separate regulatory sequences to direct production of the angiogenesis-modulating factors. Alternatively, if the nucleic acid sequences are present in the same expression vector, the nucleic acid sequences can be under the control of the same regulatory sequences. For example, two nucleic acid sequences can be under the control of a bidirectional promoter. Alternatively, nucleic acid sequences can be arranged as polycistronic sequences, the transcripts of which are processed after transcription.

Any promoter (i.e., whether isolated from nature or produced by recombinant DNA or synthetic techniques) can be used in connection with the present invention to provide for transcription of the nucleic acid sequence. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Therefore, promoter regions can vary in length and sequence and can further encompass one or more DNA binding sites for sequence-specific DNA binding proteins and/or an enhancer or silencer. Enhancers and/or silencers can similarly be present on a nucleic acid sequence outside of the promoter per se.

Transcription of the angiogenesis-modulation factors can be directed by a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the herpes thymidine kinase promoter (Wagner et al., *Proc. Natl. Acad. Sci.*, 78, 144–145 (1981)) or the Lap 2 promoter, promoters derived from SV40 or Epstein Barr virus, an adeno-associated viral promoter, such as the p5 promoter, an adenoviral promoter, such as the Ad2 or Ad5 major late promoter and tripartite leader, and the like. Non-viral promoters for use in the present invention include the regulatory sequences of the metallothionine gene (Brinster et al., *Nature*, 296, 39–42 (1982)), promoter elements from yeast or other fungi such as the Gal 4 promoter, the alcohol dehydrogenase promoter, the phosphoglycerol kinase promoter, and the alkaline phosphatase promoter. Similarly, promoters isolated from the genome of mammalian cells, such as the $\beta$-actin promoter, the muscle-creatine promoter, or the elongation factor 1$\alpha$ (EF1$\alpha$) promoter, can be employed.

Instead of being a constitutive promoter, the promoter can be an inducible promoter, i.e., a promoter that is up- and/or down-regulated in response to appropriate signals. Examples of suitable inducible promoter systems include, but are not limited to, the hypoxia-driven promoter, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed.

The regulatory sequences also can comprise a tissue-specific promoter, i.e., a promoter that is preferentially activated in a given tissue and results in expression of a gene product in the tissue where activated. A typically used tissue-specific promoter is a myocyte-specific promoter. A promoter exemplary of a myocyte-specific promoter is the myosin light-chain 1A promoter. A tissue-specific promoter for use in the present inventive vector can be chosen by the ordinarily skilled artisan based upon the target tissue or cell-type.

One of ordinary skill in the art will appreciate that each promoter drives transcription, and, therefore, protein expression, differently with respect to time and amount of protein produced. For example, the CMV promoter is characterized as having peak activity shortly after transduction, i.e., about 24 hours after transduction, then quickly tapering off. On the other hand, the RSV promoter's activity increases gradually, reaching peak activity several days after transduction, and maintains a high level of activity for several weeks. Indeed, sustained protein expression driven by an RSV promoter in an adenoviral vector is observed in all cell types studied, including, for instance, liver cells, lung cells, spleen cells, diaphragm cells, skeletal muscle cells, and cardiac muscle cells. A promoter, or combination of promoters, can be selected for use in the method of the present invention by matching its particular pattern of activity with the desired pattern and level of expression of angiogenesis-modulation factors. Thus, the nucleic acid sequences can be under the control of separate promoters having different expression profiles, e.g., at least one nucleic acid sequence is operably linked to an RSV promoter and at least one other nucleic acid sequence is operably linked to a CMV promoter. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity would be especially preferred for use in many embodiments of the present inventive method. It is also possible to select a promoter with an expression profile that can be manipulated by the investigator.

Also preferably, the adenoviral vector comprises a nucleic acid sequence encoding a cis-acting factor, wherein the cis-acting factor modulates the expression of the nucleic acid sequences. In this regard, it has been observed that the persistence of a transgene in an at least E4-deficient adenoviral vector can be modulated through the action of a cis-acting factor, such as matrix attachment region (MAR) sequences (e.g., immunoglobulin heavy chain $\mu$ (murine; Jenuwein et al., *Nature,* 385(16), 269 (1997)), locus control region (LCR) sequences, or apolipoprotein B (human; Kalos et al., *Molec. Cell. Biol.,* 15(1): 198–207 (1995)), among others. MAR sequences have been characterized as DNA sequences that associate with the nuclear matrix after a combination of nuclease digestion and extraction (Bode et al., *Science,* 255 (5041), 195–197 (1992)) and augment transcriptional activity of adjacent nucleotide sequences. Similarly, it is believed LCR sequences function to establish and/or maintain domains permissive for transcription. Many LCR sequences give tissue specific expression of associated nucleic acid sequences. Addition of MAR or LCR sequences to the expression vector can further enhance expression of angiogenesis-modulating factors.

The construction of an exogenous nucleic acid operably linked to regulatory sequences necessary for expression is well within the skill of the art (see, for example, Sambrook et al., *Molecular Cloning: A Laboratory Manual,* 2nd Ed. (1989)). With respect to promoters, nucleic acid sequences, and the like, located on an expression vector, such elements can be constructed as part of a cassette, either independently or coupled. In the context of the present invention, a "cassette" is a particular base sequence that possesses functions which facilitate subcloning and recovery of nucleic acid sequences (e.g., one or more restriction sites) or expression (e.g., polyadenylation or splice sites) of particular nucleic acid sequences. With respect to the expression of nucleic acid sequences according to the present invention, the ordinary skilled artisan is aware that different genetic signals and processing events control levels of nucleic acids and proteins/peptides in a cell, such as, for instance, transcription, mRNA translation, and post-transcriptional processing.

Protein expression is dependent on the level of RNA transcription that is regulated by DNA signals, and the levels of DNA template. Similarly, translation of mRNA requires, at the very least, an AUG initiation codon, which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Molec. Biol.,* 196, 947–950 (1987)). Also, successful expression of an exogenous nucleic acid in a cell can require post-translational modification of a resultant protein. Thus, production of a protein can be affected by the efficiency with which DNA (or RNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production, preferably the nucleic acid sequence is operatively linked to a polyadenylation site. Also, preferably all the proper transcription signals (and translation signals, where appropriate) are correctly arranged such that the nucleic acid sequence are properly expressed in the cells into which it is introduced. If desired, the expression vector also can comprise splice sites (i.e., splice acceptor and splice donor sites) to facilitate mRNA production. Moreover, if the nucleic acid sequence(s) encode a factor that is a processed or secreted protein or acts intracellularly, preferably the nucleic acid sequence further comprises the appropriate sequences for processing, secretion, intracellular localization, and the like. For example, at least one of the angiogenesis-modification factors is linked to an endoplasmic reticular signal peptide, such as that described in *Molecular Biology of the Cell,* 3$^{rd}$ Ed., Alberts et al., eds., Garland Publishing, New York (1994).

In certain embodiments, it may be advantageous to modulate production of the angiogenesis-modulating factors. An especially preferred method of modulating expression of a nucleic acid sequence comprises addition of site-specific recombination sites on the expression vector. The use of site-specific recombination to modulate transcription of a nucleic acid sequence is described, for example, U.S. Pat. Nos. 5,801,030 and 6,063,627 and International Patent Application WO 97/09439.

The present inventive method can be used to modulate neovascularization in a variety of tissues, including, for example, skeletal muscle and cardiac tissue. Modulation also can be modulated in adipose tissue (see, for example, U.S. Pat. No. 5,869,037 and International Patent Application WO 97/49827). The choice of expression vector, regulatory sequences, and angiogenesis-modulation factors will depend, in part, on the particular tissue or cell type to be transduced with two or more nucleic acid sequences encoding angiogenesis-modulation factors and the desired biological effect. The ordinarily skilled artisan has the skill to determine the appropriate expression system, regulatory sequences, and angiogenesis-modulation factors for any given tissue or cell-type. As such, the present inventive method can be used for the research or treatment of numerous diseases and ailments. For example, the present inventive method of modulating neovascularization can be used to study or treat (therapeutically or prophylactically) coronary artery disease, peripheral vascular disease, congestive heart failure (e.g., left ventricular dysfunction and left ventricular hypertrophy), neuropathy (peripheral or otherwise), avascular necrosis (e.g., bone or dental necrosis), mesenteric ischemia, impotence (or erectile dysfunction), incontinence, arterio-venous fistula, veno-venous fistula, stroke, cerebrovascular ischemia, muscle wasting, pulmonary hypertension, gastrointestinal ulcers, vasculitis, non-healing ischemic ulcers, retinopathies, restenosis, cancer, and radiation-induced tissue injury (such as that common with cancer treatment). In addition, the present invention also finds utility in the study and/or aid of wound healing (e.g., healing of ischemic ulcers), plastic surgery procedures (e.g., healing or reattachment of skin and/or muscle flaps), bone healing, ligament and tendon healing, spinal cord healing and protection, prosthetic implant healing, vascular graft patency, and transplant longevity.

In some instances, delivery of a DNA encoding an angiogenesis-modulation factor can be challenging. For example, the half-life of many angiogenic peptides is very short, the administration of high doses of angiogenic peptides is associated with hypotension, and systemic administration of angiogenic peptides can cause promiscuous induction of angiogenesis in tissues other than that which has been targeted. Furthermore, the quantity of angiogenic peptide delivered is important. The present invention involves the administration of two or more nucleic acid sequences to an animal, each nucleic acid sequence encoding at least one different angiogenesis-modulation factor. While any suitable means of administering the nucleic acid sequences to host cells can be used within the context of the present invention (e.g., intravenous administration, intramuscular administration, intraparenteral administration, topical administration, and the like), preferably, an expression vector comprising the nucleic acid sequences are administered in a localized manner, such as accomplished by directly injecting the expression vector into the target tissue or by topically applying the expression vector to the target tissue in which neovascularization is to be modulated. By the term "injecting," it is meant that the expression vector comprising two or more nucleic acid sequences encoding the angiogenesis-modulation factors is forcefully introduced into the target tissue. Any suitable injection device can be used within the context of the present invention such as that described in, for instance, U.S. Pat. No. 5,846,225. However, it is desirable that whatever means of administering the nucleic acid sequences is chosen, the modulation of neovascularization in non-targeted tissue is minimized.

For example, in the treatment of a hindlimb, two or more nucleic acid sequences can be delivered, for example, by intramuscular injection or a catheter inserted into the proximal portion of the femoral artery or arteries. For treatment of other target tissues, nucleic acid sequences encoding different angiogenesis-modulation factors can be delivered by a catheter or like device inserted sufficiently deeply into the proximal portion of the organ- or tissue-feeding artery or arteries so that gene transfer is effected substantially only into the cells of the target organ or tissue.

While administration of a dose of the expression vector can be accomplished through a single application (e.g., a single injection or a single topical application) to the target tissue, preferably, administration of the dose is via 2, 3, 4, 5, or more applications (multiple) applications to a target tissue. Preferably, 5 or more applications are administered. More preferably 8 or more applications are administered, and most preferably at least 10 (e.g., 10, 15, 20, 25, 30 or more) applications are administered. Multiple applications provide an advantage over single applications in that they can be manipulated by such parameters as a specific geometry defined by the location on the target tissue where each application is administered. The administration of a single dose of the expression vector via multiple applications can be better controlled, and the effectiveness with which any given dose is administered can be maximized. In this way, too, the undesirable effects associated with administration of a single point application of a large dose can be minimized.

The specific geometry of the multiple applications is defined by the location on the target tissue, either in two- or three-dimensional space, where each application of the angiogenic vector is administered. The multiple applications preferably are spaced such that the points of application are separated by up to about 4 cm (e.g., about 0.5–4 cm), more preferably up to about 3 cm (e.g., about 1–3 cm), and most preferably up to about 2 cm (e.g., about 1–2 cm). In three-dimensional space, a single application preferably is administered for up to about 50 cm$^3$ (e.g., about 0.5–50 cm$^3$) of target tissue, more preferably for up to about 35 cm$^3$ (e.g., about 1–35 cm$^3$) of target tissue, and most preferably for up to about 15 cm$^3$ (e.g., about 3–15 cm$^3$) of target tissue. Furthermore, the multiple applications can define any suitable pattern or specific geometry. Therefore, for example, in two-dimensional space, the multiple applications can define a square whereas in three-dimensional space the multiple applications can define a cube.

Another parameter of the multiple applications which can be manipulated is the time differential between each application. Preferably, each of the multiple applications is administered within about 10 minutes (e.g., about 0.5–10 minutes) of each other, more preferably within about 8 minutes (e.g., about 0.5–8 minutes) of each other, and even more preferably within about 6 minutes (e.g., about 1–6 minutes) of each other. Most preferably, all of the multiple applications of the single dose are administered within the aforesaid time frames. Optimally, each of the multiple applications is administered substantially simultaneously. Administration of multiple applications of angiogenic factors is further described in International Patent Application WO 98/32859.

In addition to administering a single dose of the nucleic acid sequences via multiple applications, multiple rounds of treatment (e.g., 2, 3, 4, 5, or more rounds of treatment) can be required to achieve a desired biological effect (e.g., prolonged enhancement or inhibition of neovascularization). Multiple dosing can be facilitated by manipulating the expression vector to evade the immune system. In particular, the expression vector preferably evades neutralizing antibodies and other clearance and inflammatory mechanisms.

Furthermore, administration of two or more nucleic acid sequences, each encoding at least one angiogenesis-modulation factor, to a target tissue can be accomplished either in vivo or ex vivo. Therefore, for example, a target tissue can be removed, contacted with the nucleic acid sequences, and then reimplanted. Ex vivo administration of the angiogenesis-modulators to the target tissue also helps to minimize undesirable induction of angiogenesis in non-targeted tissue.

Any suitable pharmaceutically acceptable carrier can be used within the context of the present invention to administer two or more nucleic acid sequences, and such carriers are well known in the art (see, for example, U.S. Pat. No. 6,225,289 and International Patent Application WO 00/34444). The choice of carrier will be determined, in part, by the particular site to which the composition is to be administered and the particular method used to administer the composition. Formulations suitable for injection include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous injection solutions and suspensions can be prepared from sterile powders, granules, and tablets of the kind previously described. Preferably, the pharmaceutically acceptable carrier is a buffered saline solution.

Although any suitable volume of carrier can be utilized within the context of the present invention, preferably, the nucleic acid sequences are administered in small volumes of carrier. Administration of small volumes is such that the tissue in which neovascularization is to be modulated is perfused with the nucleic acid sequences encoding angiogenesis-modulation factors and very little or no nucleic acid sequences encoding the angiogenesis-modulation factors is carried by the blood, lymphatic drainage, or physical mechanisms (e.g. gravitational flow or osmotic flow) to tissues not targeted.

The proper dosage of nucleic acids to be administered is such that neovascularization is modulated in the animal. Preferably, the dosage is sufficient to modulate the level of perfusion of a target tissue. Additionally, the dosage should be such that modulation of neovascularization in non-targeted tissue is minimized. The dosage also will vary depending upon the combination of angiogenesis-modulation factors. Specifically, the dosage will vary depending upon the particular method of administration, including the nature of the vector and nucleic acid sequences encoding and controlling the expression of the angiogenesis-modulation factors. Appropriate dosages can be determined by observing the levels of vascularization and/or perfusion in a tissue using, for example, Doppler imaging to detect blood flow or microscopy to detect changes in vessel number or quality.

For example, for an adenoviral vector comprising two or more nucleic acid sequences, each nucleic acid sequence encoding at least one angiogenesis-modulation gene product, a dose typically will be at least about $1 \times 10^6$ pfu (e.g., $1 \times 10^6 - 1 \times 10^{13}$ pfu) to a target tissue, for example, a human hindlimb. The dose preferably is at least about $1 \times 10^7$ pfu (e.g., about $1 \times 10^7 - 1 \times 10^{13}$ pfu), more preferably at least about $1 \times 10^8$ pfu (e.g., about $1 \times 10^8 - 1 \times 10^{11}$ pfu), and most preferably at least about $1 \times 10^9$ pfu (e.g., about $1 \times 10^9 - 1 \times 10^{10}$ pfu). The dose typically is for a volume of targeted tissue of about 100 cm$^3$, more typically about 150 cm$^3$.

For purposes of considering the dose in terms of particle units (pu), also referred to as viral particles, it can be assumed that there are 100 particles/pfu (e.g., $1 \times 10^{12}$ pfu is equivalent to $1 \times 10^{14}$ pu). In a single round of vector administration, using, for example, an adenoviral vector deleted of the E1a region, part of the E1b region, and part of the E3 region of the adenoviral genome about $10^7 - 10^{13}$ pu, preferably about $10^9 - 10^{11}$ pu, are administered to a targeted tissue with an estimated volume of about 150 cm$^3$. Under these conditions, a substantial level of angiogenesis-modulation factor production is achieved in the target tissue without producing detectable levels of angiogenesis-modulation factor production in distal tissues.

The following examples further illustrate the present invention but, of course, should not be construed as in any way limiting its scope.

EXAMPLE 1

This example demonstrates the modulation of neovascularization in the mouse ear model of angiogenesis using the present inventive method.

A dose of adenoviral vector comprising a nucleic acid sequence encoding VEGF$_{121}$ (Ad.VEGF, $10^{10}$ pu), an endothelial cell mitogen, was administered via injection Apo E$^{-/-}$ mice. A second adenoviral vector comprising a nucleic acid sequence encoding HBNF (Ad.HBNF), a factor associated with vessel maturation, was co-injected at various dosages ($10^{10}$, $10^9$, $10^8$, and $10^7$ pu, n=5). All injections were delivered subcutaneously at the base of the ears of anesthetized mice (12 mg/kg xylazine and 60 mg/kg ketamine, IP). Control animals received Ad.VEGF alone. Gross morphological changes to the target tissue were observed at various days post-injection. Serial laser Doppler perfusion measurements were taken at various time points post-injection. Changes in blood vessel number were identified using an Olympus BX40F microscope at 400× to examine harvested ears that had been perfusion fixed and embedded in paraffin.

At four days post-injection, administration of two nucleic acid sequences encoding different angiogenesis-modulating factors resulted in the formation of more blood vessels than the number of vessels formed in control animals. The combination of Ad.VEGF ($10^{10}$ pu) and Ad.HBNF ($10^7$ pu) resulted in the generation of 21.1% more vessels than administration of Ad.VEGF alone. Perfusion levels in mice administered Ad.VEGF and Ad.HBNF at all doses was enhanced compared to animals receiving Ad.VEGF alone.

In addition, a nucleic acid sequence encoding an endothelial cell mitogen was administered in combination with a nucleic acid sequence encoding a factor involved in vessel maturation to detect modulation of neovascularization in the mouse ear model of angiogenesis described above. Apo E$^{-/-}$ mice were administered adenoviral vectors comprising a nucleic acid sequence encoding VEGF$_{121}$ (Ad.VEGF) at a dosage of $10^{10}$ pu. A second adenoviral vector comprising a nucleic acid sequence encoding Ang-1 (Ad.Ang-1), a factor associated with vessel maturation, was co-injected at various dosages ($10^{10}$, $10^9$, $10^8$, and $10^7$ pu, n=5). Control animals received Ad.VEGF alone.

Perfusion levels were quantified using serial laser Doppler perfusion imaging. At all doses of Ad.Ang-1 administered, except $10^{10}$ pu Ad.Ang-1, peak perfusion was greater for the combination treatment than for administration of Ad.VEGF alone. Increased perfusion induced by the administration of nucleic acid sequences encoding multiple angiogenesis-modulation factors persisted until the end of the trial, Day 13.

This example demonstrates a method of modulating neovascularization comprises administering two or more nucleic acid sequences, each encoding one angiogenesis-modulation factor that acts upon a different angiogenic process. In each instance, a greater degree of neovascularization was induced by administering two nucleic acid sequences encoding different angiogenesis-modulation factors compared to neovascularization resulting from administration of one of the nucleic acid sequences alone.

EXAMPLE 2

This example demonstrates modulation of neovascularization in the rat hindlimb model by administering nucleic acid sequences encoding different angiogenesis-modulation factors with different mechanisms of action.

Adenoviral vectors comprising nucleic acid sequences encoding $VEGF_{121}$ (Ad. VEGF) or Del-1 (Ad.Del-1) were administered to six-month old male CD rats. The right femoral artery of each rat was removed seven days before administration of the nucleic acids. The rats were divided into five groups. Group 1 was administered Ad.VEGF at $4 \times 10^{10}$ pu and Ad.Del-1 at $4 \times 10^9$ pu. Group 2 was administered Ad.VEGF at $4 \times 10^{10}$ pu and Ad.Del-1 at $1 \times 10^9$ pu. Group 3 was administered Ad.VEGF at $4 \times 10^9$ pu and Ad.Del-1 at $4 \times 10^9$ pu. The rats of group 4 were administered Ad.VEGF at $4 \times 10^9$ pu and Ad.Del-1 at $1 \times 10^9$ pu. Group 5 rats were administered Ad.VEGF alone at a dosage of $4 \times 10^{10}$ pu. The adenoviral vectors were administered via two injections to the thigh and one injection to the calf of the rat hindlimb. Serial laser Doppler perfusion imaging was used to determine blood flow to foot skin. The rats were sacrificed on Day 28 post-injection for angiography and histological analysis of skeletal muscle to determine capillary and arterial numbers.

At Day 7 post-injection, tissue perfusion levels in Group 2 animals was greater than tissue perfusion levels in Group 5 control animals. At Days 14–28, tissue perfusion levels in Groups 1, 3, and 4 were all slightly higher than levels detected in Group 5 control animals. In addition, the post-mortem angiogram revealed an approximate 30% increase in angiogram units (blood vessel number) in Group 3 rats compared to the control Group 5 rats.

This example demonstrates the ability of the present inventive method to modulate neovascularization in the rat hindlimb model of angiogenesis. Like Example 1, a greater degree of neovascularization was induced by administering two nucleic acid sequences encoding different angiogenesis-modulation factors compared to neovascularization resulting from administration of one of the nucleic acid sequences alone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of modulating neovascularization in an animal, wherein the method comprises administering to the animal two or more nucleic acid sequences, each nucleic acid sequence being under the control of separate promoters having different expression profiles and each nucleic acid sequence encoding at least one angiogenesis-promoting factor that acts upon a different angiogenic process, such that the nucleic acid sequences are expressed to produce the angiogenesis-promoting factors to modulate neovascularization in the animal, wherein one of the angiogenesis-promoting factors is vascular endothelial growth factor 121 ($VEGF_{121}$).

2. The method of claim 1, wherein two or more nucleic acid sequences are present on a single expression vector.

3. The method of claim 1, wherein the expression vector is a viral vector.

4. The method of claim 3, wherein the viral vector is an adenoviral vector.

5. The method of claim 4, wherein the adenoviral vector is replication deficient.

6. The method of claim 1, wherein at least one nucleic acid sequence comprises genomic DNA.

7. The method of claim 1, wherein at least one nucleic acid sequence comprises cDNA.

8. The method of claim 7, wherein at least one nucleic acid sequence comprises genomic DNA.

9. The method of claim 8, wherein at least one nucleic acid sequence is operably linked to an RSV promoter and at least one other nucleic acid sequence is operably linked to a CMV promoter.

10. The method of claim 1, wherein at least one angiogenesis-promoting factor is linked to an endoplasmic reticular signal peptide.

11. The method of claim 1, wherein each angiogenesis-promoting factor acts upon different target molecules.

12. The method of claim 11, wherein each angiogenesis-promoting factor acts upon different cellular signal transduction pathways.

13. The method of claim 1, wherein administering to the animal comprises administering multiple applications to a target tissue.

14. The method of claim 13, wherein the target tissue is cardiac tissue.

15. The method of claim 13, wherein each of said multiple applications is administered to about 0.5–15 cm$^3$ of said target tissue and/or all of said multiple applications are administered within about 10 minutes.

16. The method of claim 1, wherein neovascularization is induced in the animal.

17. The method of claim 16, wherein a greater degree of neovascularization is induced compared to neovascularization resulting from administration of one of the nucleic acid sequences alone.

18. The method of claim 16, wherein at least one nucleic acid sequence encodes a tissue-specific angiogenic factor.

19. The method of claim 18, wherein at least one nucleic acid sequence encodes an endothelial-specific angiogenic factor.

20. The method of claim 16, wherein at least one angiogenesis-promoting factor is selected from the group consisting of an endothelial mitogen, a factor associated with endothelial migration, a factor associated with vessel wall maturation, a factor associated with vessel wall dilatation, a factor associated with extracellular matrix degradation, and a transcription factor.

21. The method of claim 1, wherein at least one angiogenic-promoting factor is selected from the group consisting of fibroblast growth factor (FGF), Del-1, an angiopoietin, tumor necrosis factor-alpha (TNF-α), midkine (MK), heparin binding neurotrophic factor (HBNF), a nitric oxide synthase (NOS), placental growth factor (PLGF), hepatocyte growth factor (HGF), tumor growth factor β (TGFβ), angiogenin, activin binding protein (ABP), connective tissue growth factor (CTGF), tissue inhibitor of metalloproteinase (TIMP), monocyte chemoattractant peptide-1 (MCP-1), COUP-TFII, HIF-1α, PR39, epidermal growth factor (EGF) and platelet derived growth factor (PDGF).

22. The method of claim 21, wherein at least one nucleic acid sequence encodes an angiopoietin, HBNF, or MCP-1.

* * * * *